(12) United States Patent
Stone et al.

(10) Patent No.: US 7,964,582 B2
(45) Date of Patent: *Jun. 21, 2011

(54) METHODS OF TREATING SKIN AND MUCOSAL TISSUE ATROPHY USING COMPOSITIONS INCLUDING TENSIONING POLYMERS

(75) Inventors: Violetta Iotsova Stone, Robinsville, NJ (US); Miri Seiberg, Princeton, NJ (US); Joseph Luizzi, Newtown, PA (US); Candelario A. Fernandez, Jr., West Hollywood, CA (US); Claudia Kaminski, Milford, NJ (US)

(73) Assignee: J&J Consumer Companies, Inc., Skillman, NJ (US)

( * ) Notice: Subject to any disclaimer, the term of this patent is extended or adjusted under 35 U.S.C. 154(b) by 183 days.

This patent is subject to a terminal disclaimer.

(21) Appl. No.: 11/084,982

(22) Filed: Mar. 21, 2005

(65) Prior Publication Data

US 2006/0210511 A1 Sep. 21, 2006

(51) Int. Cl.
*A61K 31/722* (2006.01)
*A61K 9/107* (2006.01)

(52) U.S. Cl. .................................. 514/55; 424/401

(58) Field of Classification Search ............... 424/70.13, 424/401; 514/55
See application file for complete search history.

(56) References Cited

U.S. PATENT DOCUMENTS

| | | | |
|---|---|---|---|
| 3,463,862 A | 8/1969 | Mazza | |
| 3,471,624 A | 10/1969 | Youngblood | |
| 3,862,309 A | 1/1975 | Krochock | |
| 5,621,088 A | 4/1997 | Gruber | |
| 5,700,455 A | 12/1997 | Hinterwaldner et al. | |
| 5,879,684 A | 3/1999 | Fox | |
| 5,925,337 A | 7/1999 | Arraudeau et al. | |
| 6,001,367 A | 12/1999 | Bazin et al. | |
| 6,156,804 A * | 12/2000 | Chevalier et al. ............. 514/787 |
| 6,335,023 B1 * | 1/2002 | Yu et al. ......................... 424/401 |
| 6,379,702 B1 | 4/2002 | Lorenz et al. | |
| 6,413,526 B1 | 7/2002 | Bazin et al. | |
| 2003/0206958 A1 | 11/2003 | Cattaneo et al. | |
| 2003/0215476 A1 | 11/2003 | Cassin et al. | |
| 2004/0136937 A1 | 7/2004 | Cassin | |
| 2007/0166259 A1 * | 7/2007 | Vicic et al. ................. 424/70.11 |

FOREIGN PATENT DOCUMENTS

| | | |
|---|---|---|
| WO | WO 96/19180 A1 | 6/1996 |
| WO | WO 97/25036 * | 1/1997 |
| WO | WO 98/29091 A | 7/1998 |
| WO | WO 98/29092 A | 7/1998 |
| WO | WO 03/086342 A1 | 10/2003 |
| WO | WO 2004/010965 A | 2/2004 |
| WO | WO 2005/030158 A | 4/2005 |
| WO | WO 2006/003027 A | 1/2006 |
| WO | WO 2006/056491 A | 6/2006 |

OTHER PUBLICATIONS

American Collegiate Dictionary, 3rd Edition, 1993, p. 88.*
Definition of prevent, WordNet, http://wordnet.princeton.edu, accessed online Nov. 14, 2007.*
Entry for thin skin, MayoClinic.com, http://www.mayoclinic.com/health/thin-skin/AN01688, accessed online Nov. 2, 2009.*
Entry Aging changes in skin, University of Maryland Medical Center Medical Encyclopedia, http://www.umm.edu/ency/article/004014.htm, accessed online on Apr. 20, 2010.*
Definition of prevent, Oxford English Dictionary, http://dictionary.oed.com/, accessed online on May 6, 2010.*
Data Sheet "How to put KYAMER™ PC to work for you", publicly available prior to Feb. 25, 2005.
Seino et al, "Usefulness of Water-Soluble Chitosan Derivatives as Cosmetic Ingredients", Database Chemabs [Online] Chemical Abstracts Service, Columbus, Ohio, US, accession No. 1999: 492585 & Kichin, Kitosan Kenkyu (1999) (XP002396863).

* cited by examiner

*Primary Examiner* — Shaojia Anna Jiang
*Assistant Examiner* — Jonathan S Lau

(57) ABSTRACT

The present invention features a method of treating atrophy of skin or mucosal tissue by administering to skin or mucosal tissue in need of such treatment a composition including a tensioning polymer, said method selected from the group consisting of thickening said skin or mucosal tissue, enhancing extracellular matrix production in said skin or mucosal tissue, and enhancing the barrier function of said skin or mucosal tissue.

8 Claims, 4 Drawing Sheets

METHODS OF TREATING SKIN AND MUCOSAL TISSUE ATROPHY USING COMPOSITIONS INCLUDING TENSIONING POLYMERS

BACKGROUND OF THE INVENTION

Tissue atrophy is the decrease thickness and/or functionality of the tissue. Skin atrophy, as well as other epithelial or mucosal tissue atrophy, could be induced by numerous mechanisms, including disease such as scleroderma (see, e.g., Paquette D L, et al., J. Dermatol. 30(6):438-43 (2003)), pharmaceutical agents such as glucocorticosteroids (see, e.g., Schacke H, et al., Pharmacol Ther. 96(1):23-43 (2002)), and aging (see, e.g., Whitmore S E, et al., J. Am. Acad. Dermatol. 38(2 Pt 1):248-55(1998)). The thinner and more fragile skin associated with this condition has reduced barrier function, providing less than adequate protection, and/or is more prone to dryness and wounding (see, e.g., Bryant R A, et al., Ostomy Wound Manage. 47(6):18-27(2001) and Eady R A., J Dermatol. 28(11):638-40(2001)).

Retinoids are used to increase skin thickness (see, e.g., Marks R., J Int Med Res. 18 Suppl 3:29C-34C(1990)), but potential side effects, including irritation (see, e.g., Kim B H, Toxicol Lett. 146(1):65-73(2003)) and teratogenicity (see, e.g., Azais-Braesco V, Am J Clin Nutr., 71(5 Suppl):1325S-33S(2000)) may prevent their use in certain situations. Accordingly, a need exists for a treatment from tissue atrophy.

SUMMARY OF THE INVENTION

In one aspect, the invention features a method of treating atrophy of skin or mucosal tissue by administering to skin or mucosal tissue in need of such treatment a composition including a tensioning polymer, said method selected from the group consisting of thickening said skin or mucosal tissue, enhancing extracellular matrix production in said skin or mucosal tissue, and enhancing the barrier function of said skin or mucosal tissue.

In another aspect, the invention features a product including: (a) a composition including a tensioning polymer; and (b) instructions directing the user to apply said composition to skin or mucosal tissue in order to thicken said skin or mucosal tissue, enhance extracellular matrix production in said skin or mucosal tissue, or enhance the barrier function of said skin or mucosal tissue.

In another aspect, the invention features a method of promoting a product including a composition including a tensioning polymer, wherein said method includes directing the user to apply said composition to skin or mucosal tissue in order to thicken said skin or mucosal tissue, enhance extracellular matrix production in said skin or mucosal tissue, or enhance the barrier function of said skin or mucosal tissue.

Other features and advantages of the present invention will be apparent from the detailed description of the invention and from the claims.

BRIEF DESCRIPTION OF THE DRAWINGS

A more particular description of the invention, briefly summarized above may be had by reference to the embodiments thereof that are illustrated in the appended drawings. It is to be so noted, however, that the appended drawings illustrate only typical embodiments of the invention and, therefore, are not to be considered limiting of its scope, for the invention may admit to other equally effective embodiments.

To facilitate understanding identical reference elements have been used, wherever possible, to designate identical elements that are common to the figures.

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Any percentage (%) concentration of a component is weight by weight (w/w) unless otherwise indicated.

What is meant by a "product" is a product in finished packaged form. In one embodiment, the package is a container such as a plastic, metal or glass tube or jar containing the composition. The product may further contain additional packaging such as a plastic or cardboard box for storing such container.

In one embodiment, the product contains instructions directing the user to apply said composition to skin or mucosal tissue in order to thicken said skin or mucosal tissue, enhance extracellular matrix production in said skin or mucosal tissue, or enhance the barrier function of said skin or mucosal tissue.

What is meant by "mucosal tissues" are tissues that are composed in part of cells of mesenchymal and epithelial origin. Examples of mucosal tissues include, but are not limited to, vaginal, oral, corneal, rectal, and viscero-elastic tissues. Examples of viscero-elastic tissues are those that line the respiratory track, blood vessel walls, the gastro-intestinal track, the urinal and bladder track, and the reproductive track.

What is meant by "thicken the skin or mucosal tissue" is to thicken or prevent the thinning of the skin or mucosal tissue.

What is meant by "enhancing the barrier function of skin or mucosal tissue" is enhancing or preventing the loss of the protective properties of the skin or mucosal tissue, including but not limited to the enhancing or preventing the loss of the strength of skin or mucosal tissues, the hydration of skin, and the lubrication of mucosal tissue.

What is meant by "enhancing the extracellular matrix production of skin or mucosal tissue" is enhancing or preventing the reduction of the extracellular matrix in skin or mucosal tissue, including but not limited to enhancing or preventing the reduction of collagen production.

What is meant by "promoting" is promoting, advertising, or marketing. Examples of promoting include, but are not limited to, written, visual, or verbal statements made on the product or in stores, magazines, newspaper, radio, television, internet, and the like.

For promoting the thickening of the skin or mucosal tissue or enhancing the barrier function of skin or mucosal tissue, examples of such statements include, but are not limited to, "thickens the skin," "thickens the gums," "thickens vaginal wall," "strengthens the skin," "strengthens the vaginal wall, "strengthens the gums," "plumps the skin," "restores skin thickness," "restores a post-menopausal vaginal condition", "restructures the vaginal wall," "improves the structure of vagina," "inhibits thinning of the vaginal wall," "rebuilds vaginal wall," "restructures the oral epithelial layer," "improves the structure of oral epithelial layer," "inhibits thinning of the oral epithelial layer," "rebuilds oral epithelial layer," "restructures the skin," "improves the structure of skin," "inhibits thinning of the skin," "reduces skin fragility," "rebuilds skin," "helps heal skin," "helps heal compromised, wounded, or abraded skin," "helps skin hold in moisture," "helps lubricates gums," "helps lubricate the vagina," "stimulates skin's renewal process," "skin is better moisturized," and "helps the skin stay hydrated," and "better moisturizes skin." Examples of such visual statements include pictures, drawings, or movies of skin or mucosal tissue cells depicting thickened skin or mucosal tissues and/or the thickening of the skin or mucosal tissue or the enhancing the barrier function of skin.

For promoting the enhancement of extracellular matrix production in the skin or mucosal tissue, examples of such statements include, but are not limited to, "enhances extracellular matrix production in skin," "enhances extracellular matrix production in gums," "enhances collagen production in skin" or "enhances collagen production in gums." Examples of such visual statements include pictures, drawings, or movies of skin or mucosal tissue cells depicting enhanced extracellular matrix production, such as collagen.

As used herein, "administering to skin or mucosal tissue in need of such treatment" means contacting (e.g., by use of the hands or an applicator such as, but not limited to, a wipe, tube, roller, spray, vaginal applicator, patch, tampon, toothbrush, suppository, inhaler, nasal spray, nasal dropper, eye dropper, contact lens, candy, and gums) the area of skin or mucosal tissue in need such treatment. These features may be present on the face such as under or adjacent the eyes, or on the forehead, cheeks, jowls, and neck as well as other areas of the body such as the arms and legs (e.g., cellulite).

As used herein, "composition" means a composition suitable for administration to the skin or mucosal tissue.

As used herein, "cosmetically-acceptable" means that the ingredients or compositions which the term describes are suitable for use in contact with the skin or mucosal tissue without undue toxicity, incompatibility, instability, irritation, allergic response, and the like. This term is not intended to limit the ingredient/composition to which it describes for use solely as a cosmetic (e.g., the ingredient/composition may be a pharmaceutical agent).

As used herein, "safe and effective amount" means an amount of the compound, carrier, or of the composition sufficient to induce an enhancement in tissue elasticity, but low enough to avoid serious side effects. The safe and effective amount of the compounds or composition will vary with the area being treated, the age, health and skin/tissue type of the end user, the duration and nature of the treatment, the specific compound or composition employed, the particular cosmetically-acceptable carrier utilized, and like factors.

Furthermore, the term "molecular weight" or "average molecular weight" is defined herein as number average molecular weight.

As used herein, the term "film" is meant as an at least partially continuous arrangement of matter that is remnant on and, optionally, within the skin or mucosal tissue after the composition is applied and spread thereover and a period of at least 30 minutes has elapsed at room temperature and about 50% relative humidity. Generally, the films formed by applying (e.g., spreading via hand or applicator) compositions on the skin or mucosal tissue according to embodiments of the invention described herein, are less than, on average, about 100 microns in thickness, such as less than about 50 microns.

Composition

The composition includes a tensioning polymer useful for tensioning the skin or mucosal tissue and a liquid vehicle useful for delivering the tensioning polymer to the skin or mucosal tissue. The composition may include one or more classes of other components. The various components that may be used in the composition, as well as the properties of the composition are discussed below.

Tensioning Polymer

The compositions of the present invention include a "tensioning polymer." By "polymer," it is meant a molecule that has at least three repeating monomer units and a molecular weight greater than about 3000, such as greater than about 5000, such as greater than about 10,000. The polymer may be linear or branched polymers or of various architectures such as star, hyperbranched, dendrimers, graft, comb, and the like. The polymer may be a copolymer in that it may comprise a plurality of monomer units that may be arranged in a variety of arrangements including, for example, alternating, block, or random fashion. The polymer is an organic polymer (i.e., includes carbon) and may include carbon-carbon, carbon-oxygen, carbon-nitrogen, silicon-oxygen, and/or silicon-carbon bonds linking the various monomer units.

By "film-forming polymer" it is meant a polymer that when dissolved, emulsified, or dispersed in one or more diluents, permits a continuous or semi-continuous film to be formed when it is spread with a liquid vehicle onto smooth glass, and the liquid vehicle is allowed to evaporate. As such, the polymer should dry on the glass without forming a plurality of discrete, island-like structures.

By "tensioning polymer", it is meant, a film-forming polymer that is capable of adhering to and exerting a tensioning force upon a substrate. In particular, in order to be classified as a tensioning polymer, the polymer must have a contractile force of at least about 3 grams/milligram as determined using the following contractile force test described below.

Contractile Force

Figure 1:
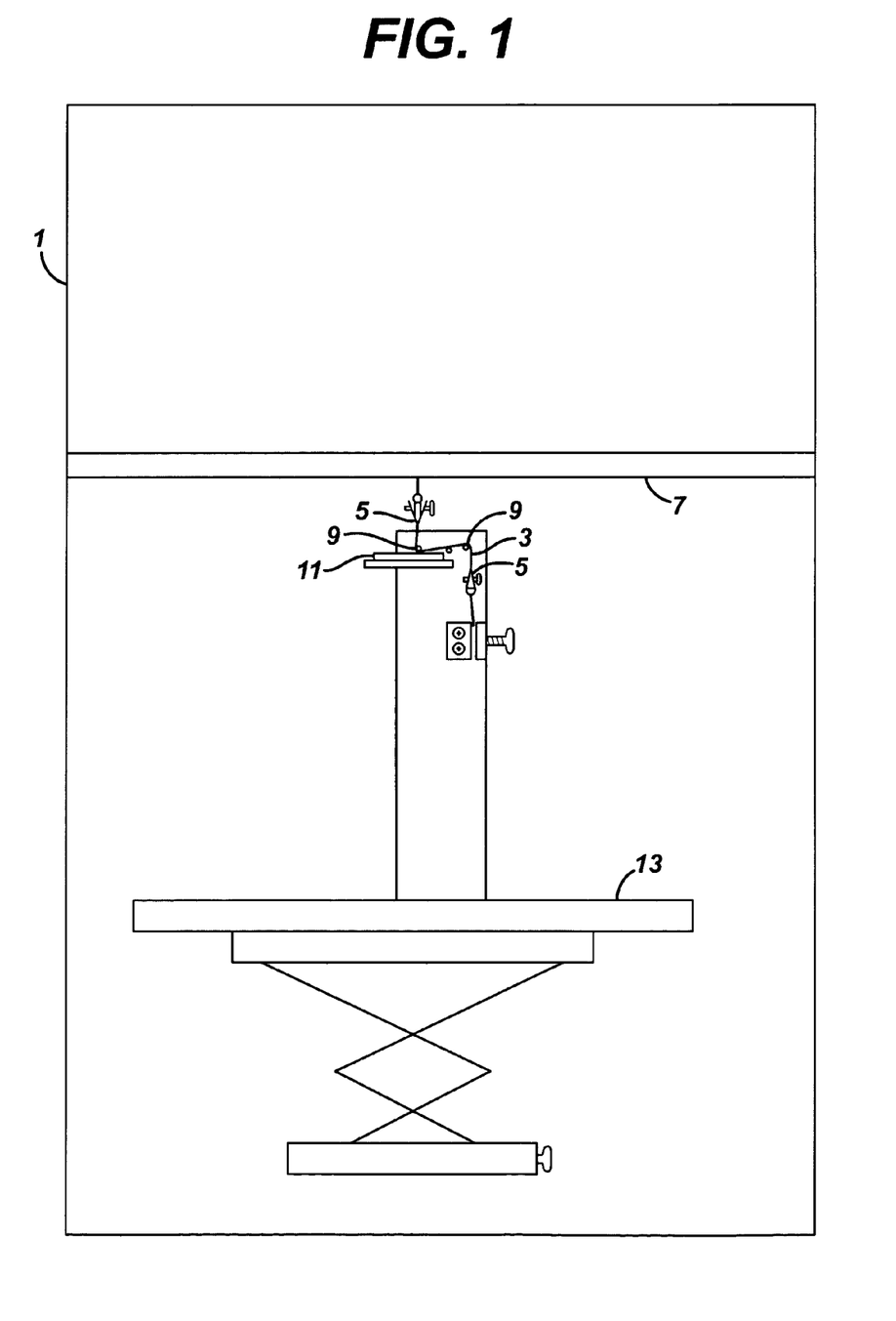
FIG. 1 is a side view of an apparatus for determining contractile force of a film-forming polymer.

The following is a test to determine the contractile force of a film-forming polymer. Referring to FIG. 1, contractile force testing is performed using a testing apparatus 1, an Instron Model 1125. The apparatus 1 is placed in a controlled temperature environment maintained at about 23+/−2 degrees Celsius and relative humidity of 50+/−2%. A substrate 3 is prepared using "Vitro Skin," a synthetic skin commercially available from IMS Inc. (Milford, Conn.). The Vitro Skin is cut into a rectangular strip 7 cm long +/−2 cm by 2 cm wide. The strip is clamped on both ends via screw clamps 5, which in turn are rigidly attached to moveable crosshead 7 of the Instron using a steel hook. The substrate 3 is arranged between two metal positioning rods 9 that are capable of rotating with little friction, such that a textured side of the substrate 3 faces up and a smooth side faces down towards the thermocouple. The positioning rods 9 are 2.7 cm apart.

A resistive heating source 11, capable of maintaining 37 degrees Celsius on the topside of the substrate 3 is placed below the substrate 3, and at a fixed distance from the substrate 3. The heating source 11 is connected to a thermocouple (not shown) in order to measure the temperature just above the substrate 3 (where the test sample will be placed). The heating source 11 is powered to provide a temperature directly above the sample that is about 37 degrees Celsius. Note that there may be a temperature gradient such that the temperature below the substrate 3, read by the thermocouple, is greater than the temperature above the substrate 3, proximate the test sample. In this case, one should increase the power to the thermocouple such that the temperature just above the substrate 3, proximate the sample is about 37 degrees Celsius.

The Instron 1125 is calibrated once before any test sequences are done on a given day. Calibration is performed as per the manufacturers instructions, by attaching a standard mass directly to the load cell. To run a test sequence, the substrate 3 is conditioned in the controlled temperature chamber by attaching the substrate 3 using the clamps 5 to the machine and placing aluminum foil around, but not contacting, the sample (to provide thermal insulation). Tension is applied to the substrate 3 via the Instron 1125 by running a test sequence using, for example, Test Works software (MTS Systems Corp. (Eden Prairie, Minn.) and selecting settings: 2 cm width, 2 inch jaw separation, 0.35 mm go to point, 0.01 inch per minute go to speed, and 8 hour hold time (total test period). The height of stage 13 is adjusted such that a force read by the apparatus 1 stays within 30-40 grams for a period of about 15 minutes. Note that after the crosshead has traveled 0.35 mm, the force reading may continue to climb, but eventually, the force reading will equilibrate (i.e., the degree of fluctuation in force (load) will diminish). As shown in illustrative FIG. 2, the maximum force for equilibration, A, is noted.

A test sample of polymer that has been dissolved or homogeneously dispersed to a weight concentration of 5% in a liquid vehicle (deionized water) within the past twenty-four hours is then brushed on to the textured side of the Vitro Skin in both lateral and transverse directions using a small paint brush (0.5 inches wide or less) to completely cover the portion of the Vitro Skin between the two positioning rods (27 mm×20 mm of substrate is treated with the test sample). The mass of the test sample is determined by subtracting the mass of the brush after it has been dipped in test sample minus the mass of the brush after one has applied the test sample to the substrate 3. This mass is the "add-on" and is recorded in milligrams (mg). The mass of the test samples applied to the substrate 3 should be between approximately 50 mg and 70 mg.

Figure 2:
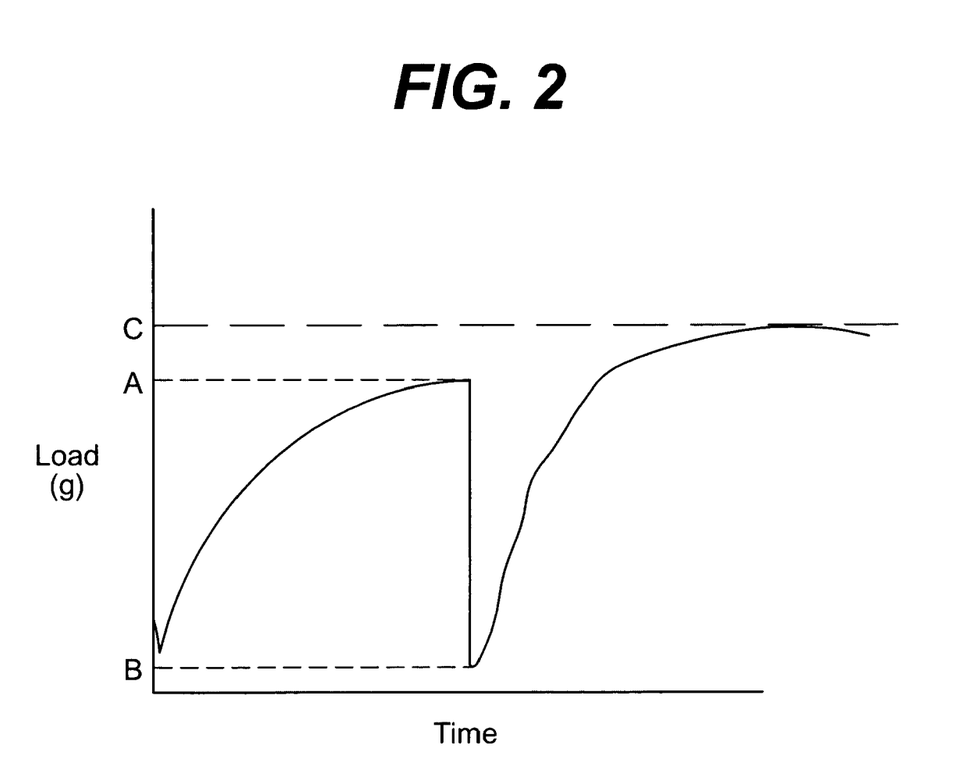
FIG. 2 is an illustrative example of a plot of load (i.e., tension) versus time for a tensioning polymer.

Upon application of the test sample, the force reading typically declines as noted in illustrative FIG. 2, such as to point B and gradually rises to a maximum that may develop within about 30 to about 100 minutes after the test sample is applied. This maximum force, C, is noted. The force differential, C-A, is calculated in grams. Add-on (in milligrams) multiplied by the weight percentage of polymer solution (5%) yields the total grams of polymer (note that liquid vehicle is subtracted from the total weight applied to the substrate). The force differential is divided by the weight (mg) of polymer to yield contractile force in g/mg of polymer. Three replicates are performed, and the average is reported as the contractile force of the polymer. The contractile force of the chitosan derivative Kytamer PC (Dow Chemical, Midland, Mich.) was found to be 16.67 g/mg, and the contractile force of chitosan from Primex EHF (Siglufjordur, Iceland) was found to be 37.92 g/mg.

While the tensioning polymer has a contractile force that is greater than 3 g/mg, it is preferable that the tensioning polymer have a contractile force greater than about 5 g/mg, such as from about 5 g/mg to about 30 g/mg, such as from about 6 g/mg to about 20 g/mg.

The polymer may have a molecular weight that is sufficiently large to promote a film to form that has enough flexibility to allow it to conform to the skin or mucosal tissue without fracturing and has a relatively large hydrodynamic volume and is capable of forming a film of sufficient thickness. However, the molecular weight is desirably not so large that when the polymer is formulated into a composition, the viscosity is so great that the product is not readily flowable or spreadable or such that the drying time is made too great. In one embodiment of the invention, the polymer has a molecular weight greater than about 100,000, such as from about 100,000 to about 600,000.

The tensioning polymer should adhere well to the skin or mucosal tissue. As such, it is desirable, but not critical, that the polymer adopt a high charge density in the composition. While it is preferable that the polymer be cationic (i.e., adopt a positive charge in solution), the polymer may be anionic (i.e., adopt a negative charge in solution) or zwitterionic (i.e., adopt both negative and positive charges in solution).

Water Resistant

It is highly desirable that the tensioning polymer be water resistant. The inventors have noted that for the tensioning polymer to be "water resistant," the tensioning polymer should possess both (1) resistance to dissolution from water when water is placed in static contact with a film of the tensioning polymer ("resistance to static dissolution") and (2) resist swelling from water when water is placed in static contact with a film of the tensioning polymer ("resistance to static swelling"). The inventors have found that tensioning polymers that possess both resistance to static dissolution and resistance to static swelling tend to be more durable when formulated and applied to the skin or mucosal tissue, and the resulting film is less prone to flaking. However, it should also be noted that the water-resistance should not be so great that the polymer is difficult to remove from the skin or mucosal tissue, such as by rubbing the polymer with mechanical force and/or cleansing solutions.

An index of water-resistance that encompasses the ability of a polymer to resist static dissolution and resist static swelling may be determined using the test described below. The test determines "water resistance index," which, in general, is desirably high for good performance as a tensioning polymer.

To determine water resistance index for a particular polymer, dissolve and/or homogeneously disperses the polymer to 5 weight percent in deionized water, and transfer the polymer dispersion onto a standard microscope slide (about 1.3 mm thick) that has been laid flat onto a hard surface. Enough dispersion is applied to the slide to coat a continuous region that extends lengthwise across the entire slide. The slide is then leaned in a nearly vertical orientation, such as against a vertical surface for about 90 minutes. The film that is cast on the slide is then examined using light microscopy.

A light microscope capable of at least 40× magnification is electronically coupled to image capture software, such as Flashpoint Video Capture (Integral Technologies, Indianapolis, Ind.), and to image analysis software such as Image Pro Plus (Media Cybernetics, Inc. Silver Spring, Md.). The software is calibrated using a standard calibration procedure so that the thickness of the film can be determined.

A magic marker is used to mark a position across the thickness of the slide (the position should be somewhat centrally located with respect to the long direction of the slide). The slide is stood on its thickness and held stationary on the stage of the light microscope and focused under 40× magnification with the marking visible within the field. The image is captured using the image capture software. The Image analysis software is opened, loading the sample photo and the calibration photo. The thickness of the film is measured in 10 locations, each of which is within about 0.5 mm of the marking. Note that if the average thickness of the film at the edge of the slide near the marking is less than about 0.03 mm, the step of applying polymer dispersion and drying is repeated 1 to 4 times in order to build up sufficient thickness. The film should be more than about 0.03 mm thick. If the average film thickness is from 0.03 mm to 0.1 mm, the average film thickness is recorded.

Keeping the slide flat, one drop of deionized water (dispensed from a capillary tube having a 1.2 mm inner diameter such as Micro-Hematocrit tubes catalog No 15401-650 available from VWR Scientific, Inc. (West Chester, Pa.) is applied to the film as near the edge of the slide and as close to the marking as possible. After waiting 5 minutes and inverting the slide to drain off any excess water, the thickness of the film is re-measured (again, 10 readings are taken within 0.5 mm of the marking, then averaged). The ratio of the average thickness after the water insult to the average thickness before the water insult is calculated. If the ratio is less than one, the film is dissolving. If the ratio is greater than one, the film is swelling. If the ratio is near one, the film is resistant to both swelling and dissolution. To assess a given polymer's water resistance index, the procedure should be repeated on an additional glass slides. The average of two water resistance indices is reported as the water resistance index. The tensioning polymer preferably has a water resistance index from about 0.9 to about 1.9, such as from about 0.9 to about 1.5, such as from about 1 to about 1.3. The water resistance index for Kytamer PC was found to be 0.98 while the water resistence index for the chitosan (Primex EHF) was found to be 5.66 and for Profam 974 (a soy protein sold by ADM Protein Specialties Division, Decatur, Ill.) was found to be 2.87, both outside the preferred range.

The inventors have found that tensioning polymers with a contractile force of at least about 3 g/mg and a water resistance index from about 0.9 to about 1.9 have particularly good performance as tensioning polymers. One particularly notable class of polymers are polysaccharides such as chitosan-based polymers having a molecular weight from about 200,000 to about 350,000. KYTAMER PC, a notable non-limiting example, is chitosan salt of pyrolidone carboxylic acid consistent with the above specifications, and commercially available from Dow Chemical of Midland, Mich.

In order to enhance the water dispersibility of the tensioning polymer in the composition while still permitting the tensioning polymer to have a high water resistance index, the tensioning polymer may be a salt (polyelectrolyte). In addition, in order to enhance the durability of the resulting film, such as through ionic bridging or via hydrogen bonding, the counter ion of the polymer salt may be selected from particular classes of compounds. For example, the tensioning polymer may be a salt of an organic acid, such as a C3-C10 organic acid, such as lactic acid, succinic acid, maleic acid, pyrolidone carboxylic acid, gluconic acid, adipic acid, benzoic acid, and caprylic acid. Also suitable are polymers that have been neutralized with an acid, such as amino acids or other acids that is capable of forming hydrogen bonds to the ionized polymer and/or are multivalent (i.e., acids having a plurality of either carboxyl or other groups that bear a negative charge in the composition), such as salts of citric acid, phosphoric acid, succinic acid, adipic acid, and the like.

The polymer may be a natural polymer, such as a protein or polysaccharide. For example, the tensioning polymer may be a protein or protein hydrolyzate, such as an extract of milk, wheat, or other cereals or of leguminous plants and of oleaginous plants, such as extracts of corn, rye, *Triticum aestivum*, buckwheat, sesame, *Triticum spelta*, pea, bean, lentil, soybean, and lupin. Other suitable proteins include water dispersable, prolamine proteins from wheat gluten ("zein proteins") available from Freeman Industries (Tuckahoe, N.Y.), gelatins, and caseinates.

In one embodiment of the invention, the polymer is a polysaccharide. Examples of polysaccharides include those derived from the polymerization of rings of D-glucopyranose, D-glucose, D-galactose, D-mannose, D-xylose or other saccharides. The polysaccharide may be derived from algae or plants, and may include, for example, starches, glycogen, cellulose, amylopectin, amylase, xylan, gum tragacanth, inulin, laminarin, and mannan. Examples of polysaccharides derived from algae or plants include cationic polysaccharides such as naturally occurring polysaccharides that have been derivatized to create cationic character, e.g. quaternization with various quaternary amine compounds containing reactive chloride or epoxide sites. Example of cationic polysaccharides include, but are not restricted to cationic guar, hydrophobically modified cationic guar, cationic hydroxypropyl guar, cationic hydrophobically modified hydroxypropyl guar, cationic hydroxyethyl guar, cationic hydrophobically modified hydroxyethyl guar, cationic hydroxyethyl cellulose and cationic hydrophobically modified hydroxyethyl cellulose.

Other suitable polysaccharides include animal and exoskeleton-derived polymers that have been modified to be made at least partially hydrophilic. Examples include polymers of natural origin derived from the body hair, nails, insect or crustacean carapaces, head hair, feathers, beaks or animal hooves or horns can be used as exoskeleton-derived polymers. Animal-derived polysaccharides include those derived from chitin, glycogen, hyaluronic acid, and galactan.

In one embodiment of the invention, to promote sufficient chain stiffness and tensioning, the tensioning polymer is a polysaccharide with beta linkages such as may be present in celluloses, alginates, and chitosan polymers. In another embodiment of the invention, the polysaccharide may be at least partially crosslinked with divalent or multivalent metals such as aluminum, calcium, magnesium, and the like or boric acid salts. Such crosslinking may render the polymer more water resistant. Other attributes of the polysaccharide (e.g., degree of substitution/neutralization) may be similar to those described in the paragraphs below, specifically relating to chitosan polymers.

Of particular note are polymers derived from chitin, in particular chitosan polymers which are deacetyl derivatives of chitin. By "chitosan polymer" it is meant a chitin that has a deacetylation of at least 25%. Deacetylation may be measured using colloid titration as discussed in K. Toei and T. Kohara, Analytica Chimica Acta, 83, 59-65 (1976). In one embodiment of the invention, the tensioning polymer is a chitosan polymer having a deacetylation greater than about 65%, such as in a range from about 75% to about 95%, such as from about 80% to about 90%. Such polymers may have particular water solubility to permit formulation in an aqueous system, yet are not so susceptible to water such that they are prone to flaking or other forms of degradation from moisture. In another embodiment of the invention, to provide a proper balance of water resistance and water solubility, the tensioning polymer is a chitosan polymer having a degree of deacetylation between about 45% and about 55%. The chitosan polymer may have a molecular weight (number average) that is in a range from about 175,000 to about 650,000, such as from about 200,000 to about 350,000.

Furthermore, the chitosan polymer may be derivatized in a manner to increase water solubility and/or enhance the ability of the polymer to form a smooth and/or continuous film on the skin/mucosal tissue and/or enhance tensioning. In one embodiment of the invention, the chitosan polymer is a chitosan salt. By "chitosan salt" it is meant a chitosan polymer that is substantially ionizable in aqueous medium. Suitable chitosan salts include those salts discussed above, including, for example carboxylic acid salts such as salts of organic acids, including C3-C10 organic acids such as lactic acid, succinic acid, maleic acid, citric acid, pyrolidone carboxylic acid, gluconic acid, adipic acid, benzoic acid, and caprylic acid, amino acids or other acids that are capable of forming hydrogen bonds, multivalent acids, and the like.

The chitosan salt is preferably derivatized on the amine functionality by neutralizing at least a portion of these amine groups (using acids such as those described in the paragraph above). As such, the chitosan salt may have a degree of substitution (DS) value greater than about 5%, such as greater than about 30%, such as from about 30% to about 50%.

Chitosan polymers may be prepared by deacetylating chitin (such as commercially available chitin from Protan Inc. of Portsmouth, N.H.) or chitosan available from Tokyo Kasei Inc. (Tokyo, Japan) using, for example sodium hydroxide, to form a chitosan polymer. Thereafter the chitosan polymer may be at least partially neutralized with an acid to form a salt. Alternatively, the chitosan polymer or salt thereof may be obtained through commercial sources such as KYTAMER L (lactic acid salt of chitosan) and KYTAMER PC (pyrrolidone caroboxylic acid salt of chitosan), commercially available from Dow Chemical (Midland, Mich.), and N-carboxy-isobutyl chitosan derivative Chito. From Bios s.r.l. (Ancona, Italy).

While it is desirable for the chitosan to be at least partially neutralized (i.e., a chitosan salt) in order to provide a high level of tensioning and a low level of tack, it is possible that the chitosan may be derivatized in a manner so as to not necessarily provide an ionizable group (i.e., salt), but is derivatized in another manner in order to otherwise enhance the hydrophilic character and/or to enhance film-formation or tensioning. Examples of suitable derivatives include etherfunctional derivatives such as alkoxylated moieties including carboxyalkyl ethers or hydroxyalkyl ethers; ester-functional derivatives, or other derivatives that provide some hydrophilic character to the chitosan polymer. Examples include carboxymethyl, carboxyethyl, hydroxylpropyl, hydroxybutyl, such as may be derivatized on the hydroxyl groups of the chitosan polymer. However, if these chitosan derivatives are chosen as the tensioning polymer, care may be taken to use relatively low molecular weight varieties such as molecular weights from about 50,000 to about 350,000 and/or in concentrations less than about 2%. Furthermore, if such tensioning polymers are chosen, other tensioning polymers, such as polymer salts may be used in conjunction with these polymers. Examples include, N-carboxyalkylation of chitosan, such as N-(carboxymethyl)chitosan or N-(carboxybutyl)chitosan sold under the name "Evalsan" by the company Jan Dekker (Nederland, the Netherlands).

Another suitable class of tensioning polymers includes proteoglycans/glycoaminoglycans, such as hyaluronic acid or sulphated varieties of proteoglycans such as dermatan sulfate, heparin-sulphate, and the like.

In another embodiment of the invention, the tensioning polymer is a synthetic polymer. Suitable synthetic polymers include, for example, polyethylene glycol, acrylic polymers, polyurethanes, polyurethane-acrylics, vinyl polymers such as polyvinyl alcohol polyvinylpyrolidone, polyurethane-polyvinylpyrrolidones, polyester-polyurethanes, polyether-polyurethanes polyacrylamides, polyureas, polysulfonates, and poly (2-ethyl-2-oxazoline) (e.g, AQUAZOL, available from ISP Specialty Polymer, Wayne, N.J.).

In one embodiment of the invention, the tensioning polymer is a crosslinked synthetic polymer such as a crosslinked polyacrylic acid that is crosslinked using a multivalent crosslinker, such as zirconium salt or other suitable metallic species. Suitable examples of externally crosslinked acrylic polymers are JONCRYL 77 and JONCRYL 74, acrylic polymers to which ammonium zirconyl carbonate crosslinking agent (e.g., BACOTE 20, commercially available from MEI Chemicals (Manchester, UK) is added in a ratio of zirconium/polyacrylic acid that is sufficient to promote crosslinking upon drying of the polymer film. JONCRYL polymers are commercially available from SC Johnson & Son, Inc. (Racine, Wis.). The crosslinked acrylic polymer may be a copolymer including at least one hydrophilic base-neutralizable monomer and at least one hydrophobic ethylenically unsaturated monomer.

The tensioning polymer is generally present in the composition in a concentration that is high enough to provide tensioning to the skin or mucosal tissue, but not so high such that either the composition is made difficult to spread about the skin/mucosal tissue or causes the composition to become unstable, and thus in dependent upon the particular polymer and the desired result. The tensioning polymer may be present in the composition in a concentration by weight that is in a range of, for example, from about 0.5% to about 20%. In order to promote sufficient tensioning, the tensioning polymer is preferably greater than about 2%, such as from about 2% to about 10%, such as from about 3% to about 7%. In particular, it has been found that once a particular concentration of tensioning polymer is reached, the amount of tensioning increases at a diminishing rate, and additional polymer may be less desirable, because of increased raw material costs and phase stability of the overall composition may be harder to achieve.

Liquid Vehicle

The composition includes a liquid vehicle useful for solublizing, emulsifying or dispersing the tensioning polymer and other ingredients in the composition. In addition, the vehicle may provide a medium by which to increase hydrodynamic volume, such that the hydrodynamic volume, may be reduced upon dissipation of the vehicle. The vehicle includes one or more compounds in a liquid or gel phase that allow the tensioning polymer to be readily spread across the skin or mucosal tissue. The liquid vehicle is generally transient (i.e., after a period of 30 minutes after application, the majority of the liquid vehicle is not incorporated into the film—it is either absorbed into the skin/mucosal tissue and/or evaporates from the skin/mucosal tissue). Suitable liquid vehicles include one or more of water, C1 to C6 alcohols (such as ethanol and isopropanol), and glycols (such as propylene glycol and hexylene glycol). In one embodiment of the invention, the liquid vehicle includes both water and a volatile liquid. By "volatile liquid," it is meant a liquid that is more volatile than deionized water. What is meant by "non-volatile" is less volatile than deionized water. The volatile liquid may be a C1 to C6 alcohol, such as ethanol or isopropanol. For example, the volatile liquid may have an evaporation rate from about 100 to about 500 (on a scale where butyl acetate has a value of 100 and deionized water has a value of about 36).

The liquid vehicle may be present in a concentration from about 30% to about 99%, such as from about 40% to about 95%, such as from about 70% to about 90%. For embodiments of the invention in which water is present, the water may be present in a concentration from about 30% to about 95%, such as from about 40% to about 90%, such as from about 40% to about 70%. For those embodiments in which a volatile liquid is present, it may be present in a concentration high enough to permit the film to set in place on the skin/mucosal tissue (e.g., become essentially non-fluid) within about 30 seconds after the film is applied. Alternatively, it may be desirable to omit the volatile solvent or to keep its level below about 1% to reduce any unpleasant odors to the user. In one embodiment of the invention, the volatile liquid is present in a concentration from about 1% to about 50%, such as from about 10% to about 45%, such as from about 20% to about 35%.

Plasticizer

The composition may include a plasticizer. By "plasticizer" it is meant a non-volatile component that modifies the mechanical properties of the film tensioning polymer and optionally provides additional benefits. If the tensioning polymer is inherently brittle, the composition may include one or more plasticizers (or film modifiers) to reduce the tendency of the film to crack or flake. These may be compounds in monomeric, oligomeric, or even polymeric form (note that a polymer may only qualify as a plasticizer if it does not qualify as a tensioning polymer, as discussed above), and may have a molecular weight from about 100 to about 175,000 such as from about 100 to about 5000. In one embodiment of the invention, the plasticizer is hydrophilic and/or hygroscopic (i.e., absorb or retain some moisture from ambient surroundings or from the composition) in order to enhance plasticity, flexibility, moisturization, and/or comfort to the user. Suitable hydrophilic and/or hygroscopic plasticizers include those with hydroxyl groups such as glycols such as propylene glycol and hexylene glycol; glycol ethers such as diethylene glycol ethyl ether or methyl ether, ethylene glycol ethyl ether or butyl ether, propylene glycol methyl ether or phenyl ether, dipropylene glycol ethyl ether or butyl ether, tripropylene glycol butyl ether or methyl ether; and glycerol esters. Other suitable plasticizers include acid esters such as citrates, phthalates, adipates, carbonates, tartrates, and phosphates.

Other suitable plasticizers may be considerably hydrophobic such as oils. By "oils" it is meant a hydrophobic compound (hydrocarbon-based or silicone-based) that is liquid at room temperature, including mineral oils (such as petrolatum and the like), vegetable oils (such as essential and volatile oils, including terpenes, aldehydes and ketones, phenols, and esters), esters such as fatty acid esters of glycerol, and oxyethylenated oils such as oxyethylenated castor oil. Other suitable plasticizers include emulsifiers such as oil-in-water emulsifiers or water-in-oil emulsifiers, such as non-ionic surfactants or waxes and other mixtures of esters. Other suitable plasticizers include hydrocarbon waxes. One suitable hydrocarbon wax is cetyl dimethicone, available as Abil Wax 9801 (Degussa Corp of Essen, Germany).

Silicone plasticizers are particularly noteworthy plasticizers in that they may contribute to spreadability, water-resistance, and/or reduced tack in the film. Suitable silicone plasticizers include silicone fluids that may be less volatile than water under standard conditions, such as dimethicone and cyclopentasiloxane; silicone waxes such as DC 2501, a water dispersible silicone glycol copolymer wax; and oxyethylenated silicone oils; silicone elastomers. Dow Corning 7-3101 (Dow Corning of Midland, Mich.) is a silicone elastomer is commercially available as a mixture with silicone oils as a "high internal phase emulsion." Dow Corning 7-3101 has a particle size of about 12-16 microns); and silicone polymers or copolymers such as polysilicone-11, suitable silicone polymers or copolymers mixed with silicone oils include USG-103, KSG-210, and KP-545, commercially available from Shin-Etsu (Tokyo, Japan).

Other plasticizers of particular note include propylene glycol, hexylene glycol, sodium polyaspartate, glycerin, hyaluronic acid, urea, plant extracts such as Imperata cylindrical root extract, polyquaternium compounds such as polyquaternium-51, a copolymer made from 2-methacry-loyloxyethyl phosphorylcholine and butyl methacrylate (commercially available as Lipidure PMB); and Advanced Moisture Complex, a blend of glycerin, sodium hyaluronate, sodium pyrrolidone carboxylic acid, urea, and trehalose, commercially available from Collaborative Laboratories (Stony Brook, N.Y.), spreading agents such as dimethicone copolyols, cyclopentasiloxane, esterified oils such as PEG-modified olive oil, and alkali metal salts of pyrolidone carboxylic acid; and other silicone plasticizers.

Note that while the above materials are described as plasticizers, these materials may be "multi-functional" in that they also serve additional functions, including, for example, emolliency/spreadability, wetting/surface tension reduction, moisture retention, emulsification, fragrance, tensioning, thickening, and/or gloss reduction/mattifying.

One example of multi-functional ingredients that may function as plasticizers are thickeners such as clays and thickening polymers. Note that depending upon how the particular polymer or thickening agent performs in the contractile force test (described above), the polymer/thickener may also be classified as a tensioning polymer. Note also that anionic thickeners may be omitted from the composition if the tensioning polymer is cationic, in order to reduce the likelihood of shelf instability.

Thickeners include clays such as bentonite or synthetic clays such as magnesium aluminum silicate (available as LAPONITE XLG (Southern Clay Products, Gonzales, Tex.); naturally occurring polysaccharides such as Xanthan gum (e.g. KELTROL CG available from CP Kelco, San Diego, Calif.), an extracellular polysaccharide made by the bacteria xanthomonas campestris. Xanthan gum has a cellulose-like backbone (beta-1,4-poly-glucose) with trisaccharide branches (stubs) on alternate monomers on the backbone. Other naturally occurring polysaccharides that may be suitable include alginates, a seaweed gum (or derivatives thereof) extracted from kelp, a linear polysaccharide containing two types of residue (i.e., a co-polymer): b-D-mannopyranosyluronic acid and a-L-gulopyrasonic acid; pectin, extracted from the cell walls of higher plants; and carageenan, a seaweed gum a linear D-galactopyranosyl chain with alternating 1,3 and 1,4 links; cellulose ethers including methyl cellulose, carboxymethyl cellulose, hydroxy propyl methyl cellulose, hydroxyethyl cellulose, hydroxypropyl cellulose, and ethyl hydroxyethyl cellulose, Gafquat HS-100, Polyquaternium-28, polyquaternium-4, polyquaternium-10, polyquaternium-51, sodium alginate, agarose, amylopectins, amyloses, arabinans, arabinogalactans, arabinoxylans, carrageenans, gum arabic, cellulose derivatives such as methylcellulose, hydroxypropylmethylcellulose, hydroxyethyl cellulose, carboxymethylcellulose, carboxymethylguar gum, carboxymethyl(hydroxypropyl)guar gum, hydroxyethylguar gum, hydroxypropylguar gum, cationic guar gum, chondroitins, cocodimonium hydroxypropyl oxyethyl cellulose, colominic acid [poly(N-acetyl-neuraminic acid], corn starch, curdlan, dermatin sulfate, furcellarans, dextrans, cross-linked dextrans known as dextranomer (Debrisan), dextrin, emulsan, flaxseed saccharide (acidic), galactoglucomannans, galactomannans, glucomannans, glycogens, guar gum, or hydroxyethylstarch, hydroxypropylstarch, hydroxypropylated guar gums, gellan gum, glucomannans, gellan, gum ghatti, gum karaya, gum tragacanth (tragacanthin), heparin, hyaluronic acid, inulin, keratan sulfate, konjac mannan, laminarans, laurdimonium hydroxypropyl oxyethyl cellulose, liposan, locust bean gum, mannans, nigeran, nonoxylnyl hydroxyethyl cellulose, okra gum, oxidized starch, pectic acids, pectins, polydextrose, potato starch, protopectins, psyllium seed gum, pullulan, sodium hyaluronate, steardimonium hydroxyethyl cellulose, raffinose, rhamsan, tapioca starch, welan, levan, scleroglucan, stachyose, succinoglycan, wheat starch, xanthan gum, xylans, xyloglucans, polyacrylates such as CARBOPOL (available from Noveon), polyacrylamides; and mixtures thereof.

The amount of plasticizer, if included, may be sufficiently high to reduce flaking that would otherwise occur in the film, but is not too high such that skin/mucosal tissue tensioning of the film is reduced or such that the film is too tacky. The ratio of the plasticizer to the total solids content of the film may be from about 30% to about 90%, such as from about 50% to about 80%. Note that the total solids content (% solids) of the film is calculated by adding the weight percentage concentrations of all of the ingredients except those that have an evaporation rate greater to or equal than deionized water (i.e., those components that are part of the "Liquid Vehicle").

In order to prevent the film from being too tacky, the molecular weight of the plasticizer may be kept below about 500. Particularly tacky materials such as those plasticizers having multiple hygroscopic functional groups (e.g., hydroxyls) and having a molecular weight greater than about 1000 may be avoided or be present in the composition in concentrations less than about 0.5%.

Mattifying Agents

In order to reduce the shine and/or glossiness of film, mattifying agents may be incorporated (e.g., by suspension) into the composition. The mattifying agents employed may be particulate materials. By "particulate materials" it is meant moieties that do not dissolve in the liquid vehicle, but rather and form discrete units greater than about 0.2 microns, but less than about 1000 microns, such as may be suspended within the composition. The particulate material may be a hard inorganic particulate (without or without hydrophobic coatings or surface modification) including, for example, oxides such as oxides of silica (including fumed silica, precipitated silica, and colloidal silica), titanium dioxide, or other chemically produced or mined oxides, talc, mica, or aluminosilicates, and the like.

The particulate material may be a fine particulate. By "fine particulate" it is meant a particulates that is generally capable of forming fine, discrete domains (e.g. less than about 200 microns, such as from about 0.2 microns to about 100 microns, such as from about 1 micron to about 50 microns, such as from about 1 micron to about 20 microns in the film).

In another embodiment of the invention, the mattifying agent is a hydrocarbon or silicone polymer that modifies the morphology of the film, such as, for example, a cross-linked polymer such as an elastomer, such as a silicon elastomer or a hydrocarbon or nitrogen-containing elastomer (e.g., acrylic, urethane, and the like). Without wishing to be bound by theory, it is believed that the elastomer forms flexible domains in the film that disrupt the surface of the film to provide matting. The silicone elastomer may be carried in a silicone oil to facilitate stabilizing the silicone elastomer in the composition as well as to enhance spreadability of the composition. One suitable silicone elastomer that may be used is a dimethicone crosspolymer in a mixture further comprising cyclopentasiloxane and dimethicone. An example of such a mixture is Dow Corning 7-3101, from Dow Corning of Midland, Mich.

Other particulates of note include inorganic particulates such as silica gels, aluminum silicates, and fumed silicas such as surface modified or silylated fumed silicas such as Aerosil R812S available from Degussa AG (Piscataway, N.J.).

Other particulate materials that may be suitable include mica coated with titanium dioxide (available as "Flemenco Summit Red" from Englehard Corporation of Iselin, N.J.), ground organic particles such as oyster shells, walnut shells, silk protein particles, resins such as nylon or acrylates, and the like. However, if particulates such as these are included in the composition, and the particle size is large, such as 200-500 microns or greater, it may be desirable to limit the concentration of such particles to less than about 1%, such as less than about 0.5%.

If particulate materials, such as fine particulates are included in the composition, the proportion of the particulate to the total solids content of the film may be greater than about 0.5%, such as from about 0.5% and about 20%, such as from about 1% to about 10%, such from about 1% to about 4%. Surprisingly, it is possible to include particulate materials in the composition without either causing the composition to be phase unstable (e.g., such as via settling of the particles) or creating a grainy texture to the composition when it is used.

Opacifying Agents

In one embodiment, the composition contains one or more opacifying agents. What is meant by an opacifying agent is an agent added to reduce the clear or transparent appearance of the composition. Examples of opacifying agents include, but are not limited to, tin oxide, iron oxide, methyl methacrylate crosspolymer, and ethylene/acrylic acid copolymer.

Benefit Agents

In one embodiment of the invention, the composition is free of benefit agents. Alternatively, various benefit agents may be included in the composition. What is meant by an "benefit agent" is a compound (e.g., a synthetic compound or a compound isolated from a natural source) that has a cosmetic or therapeutic effect on the tissue including, but not limited to, lightening agents, darkening agents, anti-acne agents, anti-microbial agents, anti-inflammatory agents, antifungals, external analgesics, photoprotectors, antioxidants, keratolytic agents, vitamins, astringents, hair growth inhibitors, anti hair-loss agents, hair growth promoters, hair removers, skin-firming agents, anti-aging agents such as anti-wrinkle agents, allergy inhibitors, antiseptics, external analgesics, antipruritics, antihistamines, antiinfectives, anticholinergics, extracellular matrix enhancing agents, vasoconstrictors, vasodilators, wound-healing promoters, peptides, polypeptides and proteins, enzymes and enzyme inhibitors, sensate, anti-oxidants, keratolytics, sunscreens, anti-edema agents, and combinations thereof.

In one embodiment, the benefit agent is selected from the group consisting of hydroxy acids, benzoyl peroxide, D-panthenol, octyl methoxycinnimate, oxybenzone, titanium dioxide, octyl salicylate, homosalate, avobenzone, carotenoids, free radical scavengers, spin traps, retinoids and retinoid precursors such as retinol and retinyl palmitate, ceramides, polyunsaturated fatty acids, essential fatty acids, enzymes, enzyme inhibitors, hydrogen peroxide, minerals, hormones such as estrogens, steroids such as hydrocortisone, 2-dimethylaminoethanol, copper salts such as copper chloride, peptides containing copper such as Cu:Gly-His-Lys, coenzyme Q10, amino acids such a proline, vitamins, lactobionic acid, acetyl-coenzyme A, niacin, riboflavin, thiamin, ribose, electron transporters such as NADH and FADH2, and botanical extracts such as from aloe vera, oatmeal, feverfew, malva, bearberry, Cotinus coggygria, chamomille, thyme, and soy, and derivatives and mixtures thereof. The benefit agent will typically be present in the composition of the invention in an amount of from about 0.001% to about 20% by weight of the composition, e.g., about 0.005% to about 10% such as about 0.01% to about 5%.

Examples of vitamins include, but are not limited to, vitamin A, vitamin Bs such as vitamin B3, vitamin B5, and vitamin B12, vitamin C, vitamin K, vitamin E such as alpha, gamma or delta-tocopherol, and derivatives and mixtures thereof.

Examples of hydroxy acids include, but are not limited, to glycolic acid, lactic acid, malic acid, salicylic acid, citric acid, and tartaric acid. Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), different types of tocopherols (e.g., alpha-, gamma-, and delta-tocopherols and their esters such as acetate) and their mixtures, tocotrienols, and ubiquinone. Natural extracts containing antioxidants suitable for use in the compositions of this invention, include, but not limited to, extracts containing flavonoids, isoflavonoids, and their derivatives such as genistein and diadzein (e.g., such as Soy and Clover extracts, extracts containing resveratrol and the like. Examples of such natural extracts include grape seed, green tea, pine bark, and propolis.

Benefit agents of particular note are skin rejuvenating agents such as skin firming agents such as alkanolamines including dimethylaminoethanol ("DMAE"); neo-collagen promoters such as sugars including lactose and mellibiose, retinoids such as retinol, and copper-containing peptides; ascorbic acid and its derivatives; and soy extracts.

In one embodiment of the invention, the composition includes an alkanolmaine such as DMAE and an anionic polymer, such as, for example, sodium polystyrene sulfonates to form a salt that is formulated at a pH suitable for application to the skin. In such as manner, the DMAE may be gradually released from the film and diffuse into the skin to provide continuous lifting and firming thereto.

Mineral Water

The compositions of the present invention may be prepared using a mineral water, for example mineral water that has been naturally mineralized such as Evian® Mineral Water (Evian, France). In one embodiment, the mineral water has a mineralization of at least about 200 mg/L (e.g., from about 300 mg/L to about 1000 mg/L). In one embodiment, the mineral water contains at least about 10 mg/L of calcium and/or at least about 5 mg/L of magnesium.

Other Ingredients

In addition to those components listed above, other additives may be incorporated into the composition in concentrations such that they do not detract from tensioning, stability, and other aspects of product performance. Such ingredients include, for example, cosmetically acceptable preservatives, pH adjusters, chelating/sequestering agents, viscosity modifiers such as sodium chloride; dye, and fragrance.

Nature and Properties of the Composition

The composition may take one of various forms such as a gel or a liquid into which the various ingredients may be dissolved, dispersed, or emulsified, or suspended. The composition may be, for example, a hydroalcoholic system, an oil-in-water emulsion, or a water-in-oil emulsion.

The inventors have surprisingly noted that particular compositions in which the oil is the most exterior phase of the composition such as a water-in-oil emulsion or an oil-in-water-in-oil emulsion, wherein the composition includes at least about 1% of tensioning polymer, and optionally having one or more particular attributes may be particulary desirable. For example, the composition may be a water-in-oil emulsion in which the oil phase comprises at least about 15%, such as at least about 20% of the composition, such as from about 20% to about 40%. In one embodiment, the oil phase comprises at least about 10% such as at least about 40% silicones. The inventors have found that an oil-in-water emulsion having one or more of these attributes achieved sufficient tensioning and water-resistance, as well as spreadability and aesthetics. This is particularly surprising since it would not be intuitive for a composition in which the oil is the exterior phase, particularly in the presence of organosilicones, to show tensioning. What is meant by the "oil phase" are the ingredients of the formulation which are not soluble or dispersible in water.

In one embodiment, the composition may be a substantially clear. By substantially clear it is meant transparent or translucent, when observed through a layer having a thickness of less than about 10 cm. The substantially clear composition may be such that any particles are less than about 300 nm in size. Alternatively, the composition may be opaque, such as an emulsion or dispersion in which internal emulsified phase or dispersed matter has a particle size greater than about 300 nm. In order to prevent the film from imparting any particular color to the skin or mucosal tissue, the composition may be colorless or substantially free of colored pigments or dyes such as may be typically found in make-up or color cosmetics. In another embodiment of the invention, the composition includes colored pigments or dyes in order to function as a combination of make-up foundation and tensioning composition.

The composition may have a pH that is from about 3 to 7, such as from about 5 to about 6.5. The total level of solids in the composition is variable, but may be greater than about 10%, such as from about 12% to about 20%, such as from about 15% and about 20%.

Yield Point

In one embodiment, the yield point of the composition is from about 15 Pa to about 50 Pa. It may be desirable to have such a yield point for two reasons: 1) to provide resistance to flow down vertical surfaces of the skin or mucosal after application and 2) to maintain suspension of particulate material that may be present in the composition.

Note that by the term "yield point" in this specification, it is meant the ability of the composition to resist flow under stress at very low shear rates. A composition with a yield point does not begin to flow until the stress applied to the systems exceeds the yield point and the structure of the system is disturbed. When the stress is below the yield point, the system displays elastic behavior, or 'solid-like' behavior.

The yield point may be determined by an oscillatory stress sweep using a TA Instruments AR 2000 Rheometer (New Castle, DE). Parallel plate geometer with 0° and a diameter of 40 mm are used. The gap between the plates is set to 400 micron. All measurements are preformed at 25° C., and a solvent trap is used to minimize evaporation during the experiment. The oscillatory stress is increased from 0.010 Pa to 15920 Pa, while the frequency is held constant at 1.00 Hz. Nine Data points are collected over each decade of the oscillatory stress sweep. The yield point is defined as the stress at which a discontinuity in the strain occurs.

Viscosity

The composition should be spreadable on the skin or mucosal tissue such that the composition can be readily spread across the skin/ mucosal tissue or portions thereof into a thin film with reasonable effort. In one embodiment, the composition has a viscosity that is less than about 200,000 cps, such as less than about 100,000 cps, such as from about 30,000 cps to about 100,000 cps, such as from about 10,000 cps to about 90,000 cps, such as from about 30,000 cps to about 60,000 cps.

"Viscosity" as discussed in this specification is measured using a Brookfield viscometer and selecting an spindle LV4 at a speed of revolution of 6.0 RPM. Readings are taken within the viscometer every 30 seconds. Once a reading stops varying more than +/−3% versus the previous reading, no more readings are taken, and the last reading is reported as the viscosity.

Product, Package and Method of Use

The composition may be sold as a product. The product may include a conventional bottle, jar, or other container with a top or lid through which the composition may be accessed by dabbing the composition onto the hand and spreading the composition onto the skin or mucosal tissue. The composition is generally spread into a thin film on the skin or mucosal tissue. Over time the composition is generally partially absorbed into the skin or mucosal tissue and partially evaporated from the skin or mucosal tissue. The product may include a device or applicator to topically apply the composition to the skin such as a foam, sponge, or brush, a swab, a spray nozzle (e.g., aerosol), a twist-up tube, a wand and the like.

Figure 3:
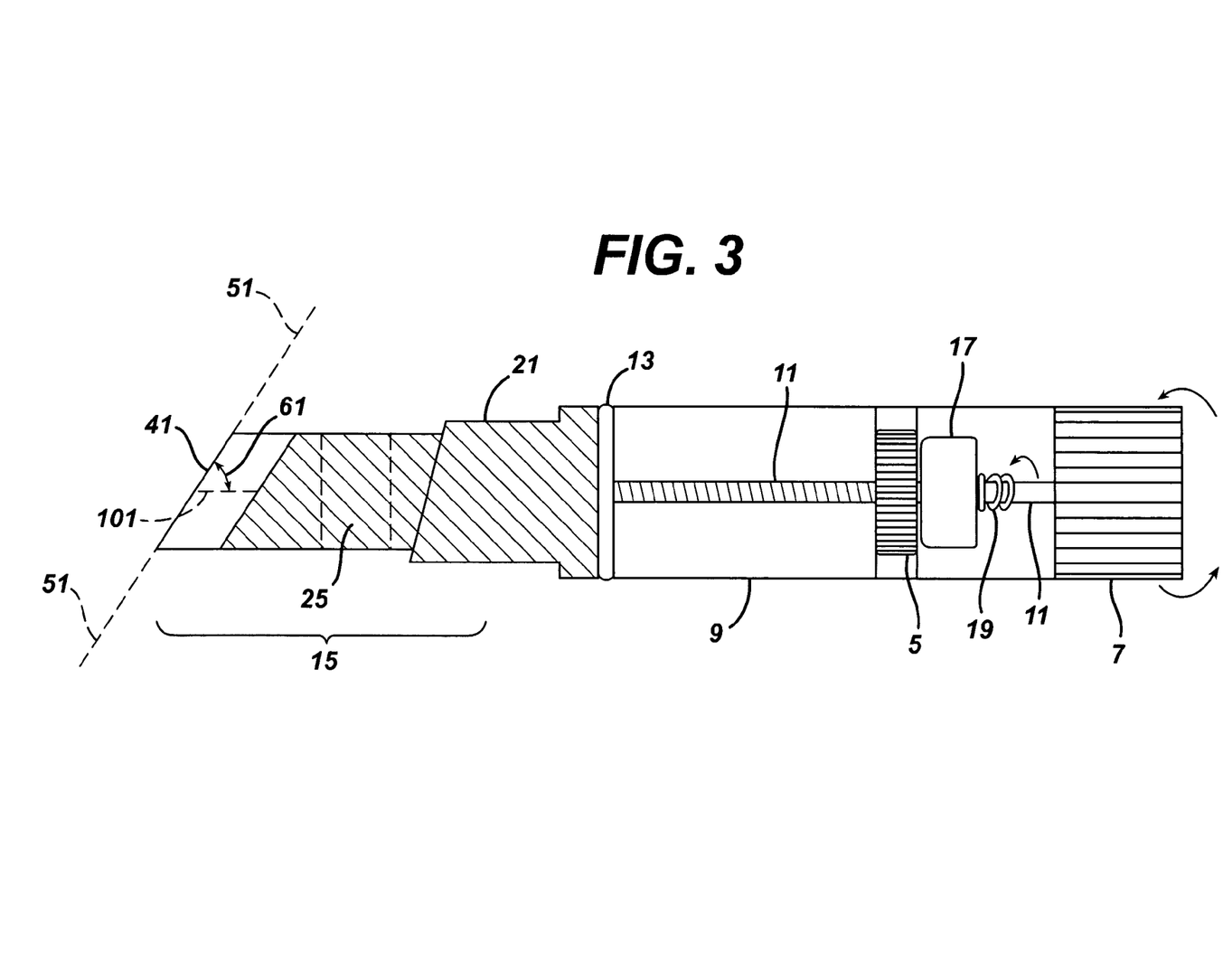
FIG. 3 is a cross-sectional view of a device consistent with embodiments of the invention described herein.

In one embodiment of the invention, the product includes an applicator that includes a surface for contacting the skin. One suitable applicator is a "stick applicator" shown in cross-section in FIG. 3. Applicator 3 is an elongate wand or pencil-type applicator for applying a composition to the skin. Applicator 3 includes a cylindrical shell 5 that includes a distal portion 7 and a proximal portion 9. In FIG. 3, shell 5 is depicted as transparent in order to see the contents inside. The proximal portion 9 terminates in a head portion 15. The distal portion 7 is rotatably coupled to an inner threaded rod 11 that is concentric with the shell 5. The threaded rod 11 is coupled to a plunger 13 that may be advanced towards the head portion 15 by rotating the distal portion 7. Rotation of the distal portion 7 (as indicated by the arrows in FIG. 3), results in a discrete rotation of the rod 11 via a transmission assembly 17 that may include a spring 19, gears, or other mechanical elements known to those skilled in the art of hand-held applicators for dispensing liquids and gels.

The composition (shown in crosshatching in FIG. 3) is positioned within a reservoir such as a hollow tube 21 (shown in phantom in FIG. 3) within the shell 5, in a proximal direction (i.e., towards the head portion 15) from the plunger 13. As the distal portion 7 is rotated, the plunger 13 advances, thereby urging the composition to move towards the head portion 15. By controlling the spacing of the threads on the rod 11, the discrete distance that the plunger 13 is advanced may be controlled. For example, the plunger 13 may advance about 0.5 mm when the distal portion 7 is rotated 360 degrees.

The inventors have noted that for the device of the present invention, it is particularly important to deliver the composition at a controllable dose in order to prevent the film from being applied to thick, which likely leads to cracking and flaking. This is particularly true considering the typical rheology of compositions used is one of "shear thinning." Such rheology is generally preferred by the end-user, but often leads to additional product traveling through the device even after the user stops causing the device to deliver more composition (e.g., turning the distal portion 7). In order to deliver precise and controlled amounts of composition, the device may provide an auditory "click" each time the distal portion 7 is rotated, for example, every 45 degrees. Such controlled delivery may advance the plunger 13 such that a volume of from about 0.001 cubic centimeters (cc) to about 0.01 cubic centimeters of composition per discrete motion (or "click") is extruded through a skin-contactable surface 41. This is helpful in that a typical end-user may want to "click" 2 or 3 times, dosing from about 0.025 to about 0.25 cc (such as from about 0.05 cc to about 0.1 cc) and apply the composition to the skin via the device. The inventors have found that such dosing helps to provide an appropriate film thickness.

The tube 21 extends into the head portion 15, and upon urging from the plunger 13, the composition travels from the tube 21 and through an optional shearing insert 25 (shown in phantom in FIG. 3) that is positioned within the tube 21 in the head portion 15. The optional shearing insert 25 may be advantageous to use in conjunction with compositions that are shear thinning. The shearing insert 25 is a medium of fine pores, such as, for example, may be formed from closely packed polyethylene rods, spheres and the like. Alternatively, the shearing insert 25 may be formed from a screen of grid of fine mesh. In one embodiment, the shearing insert 25 has an average void diameter of 50 microns to about 500 microns, such as from about 100 microns to about 200 microns (e.g., 125 to about 175 microns). The shearing insert 25 may have a void volume (% open area) that is from about 10% to about 70%, such as from about 20% to about 60%, such as from about 30% to about 40%. By way of example, one suitable insert 25 comprises plastic (e.g., polyethylene) spheres and has an average void diameter of 150 microns and 40% open area.

Another suitable insert 25 comprises polyethylene spheres and has an average void diameter of 130 microns and 30% open area. The exemplary inserts materials are available from Porex Porous Group (Fairburn, Ga.) and may be cut or otherwise fabricated to a size that fits snugly within the tube 21, such that the composition is forced to travel there through.

Extruding the composition through the shearing applicator 25 may allow one to use a composition of relatively high viscosity (thereby retarding the settling of any particulate materials that may help provide low gloss), yet the composition is sheared to a lower viscosity prior to application for good film formation on the skin.

Figure 4:
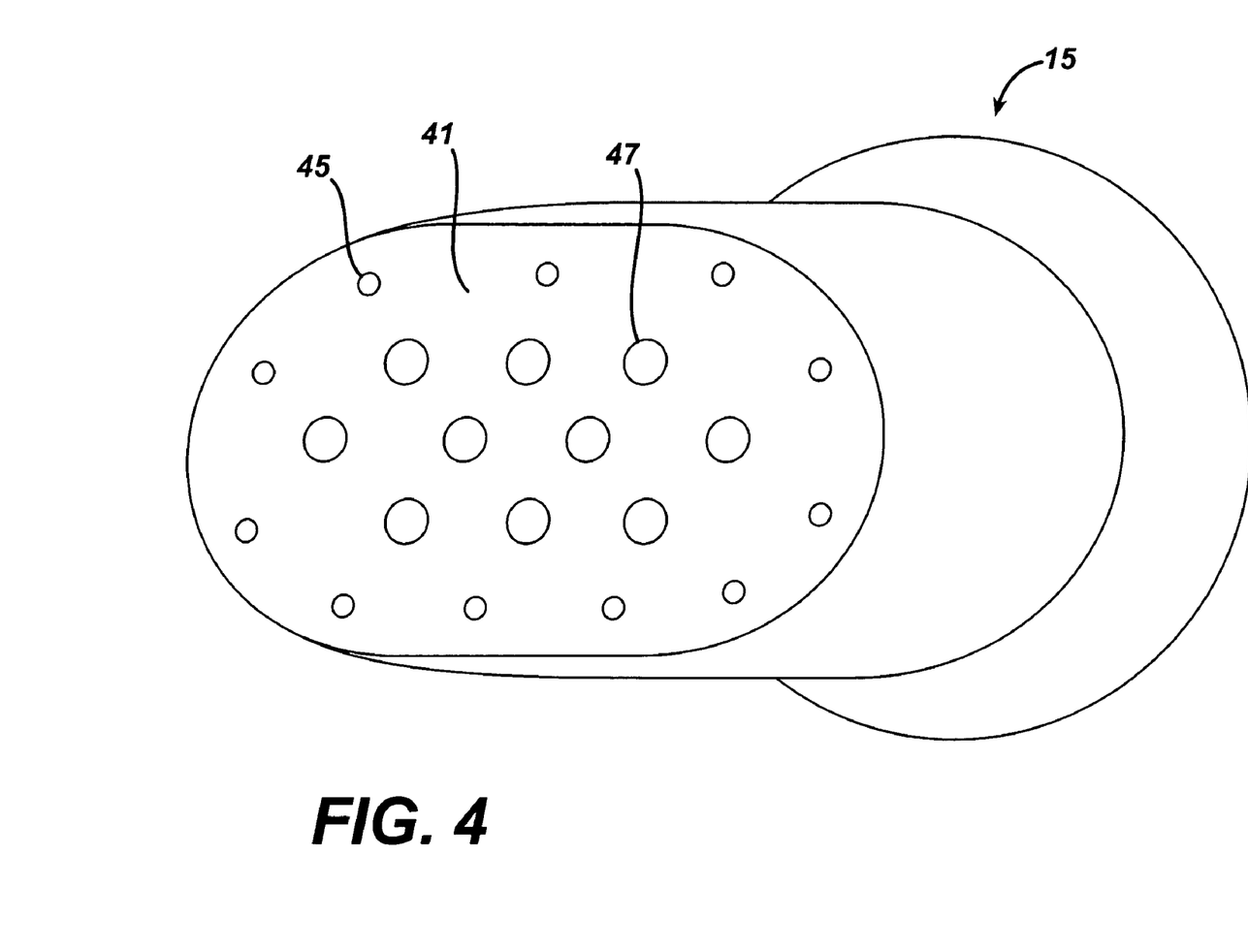
FIG. 4 is a partial, perspective view of the head portion of the device of FIG. 3, revealing a pattern of openings formed in a skin contactable surface.

FIG. 4 shows a partial perspective view of the head portion 15. The composition upon urging from the plunger 13 continues through the tube 21 then passes into the head portion 15. The head portion 15 may be attached to the remainder of the proximal portion 9 via snap fitting or other means. The composition is then urged (e.g., extruded) through the plurality of outer openings 45 and inner openings 47 across a plane 51 defined by the skin-contactable surface 41. Examples of the shape of opening include, but are not limited to, circles, ovals, rectangles, and the like. The skin-contactable surface 41 is placed against the skin (e.g., skin in need of treatment) of the user in order to contact the skin with the composition. The skin-contactable surface 41 may be rubbed or glided across the skin using the skin-contacting surface 41 of the applicator 3 to distribute the composition across the skin.

In one embodiment of the invention, the skin-contactable surface 41 is angled (i.e., is not perpendicular to an imaginary line 101 going lengthwise through the center of the shell 5). The angled skin-contactable surface 41 facilitates contacting various surfaces and contours of the skin on the face such as near the eyes, nose, and the like. In particular, an angle 61 of the surface 41 may be from about 35 degrees to about 60 degrees in order to facilitate such contact.

In addition, as shown in FIG. 4, in order to provide a pleasant softness to the skin-contactable surface 41, the skin-contactable surface 41 may be coated or layered a soft, comfortable, resilient material, such as sleeve of fibers formed polyethylene, nylon, polyester, cotton and the like.

The outer openings 45 and inner openings 47 may be considerably larger than the pores of the shearing insert 25, but in one embodiment are less than about 4 mm$^2$, such as less than about 1 mm$^2$. The inventors have noted that it is particularly desirable to have the device provide (i) a visual cue that what appears to the end-user as sufficient composition has been extruded through the outer openings 45 and inner openings 47 and (ii) that this "visually sufficient" amount is not so great that it results in the deposition of a film that is too thick and flaking or cracking of the film on the skin results. As such, the inventors have noted that it is desirable that the outer openings 45 and inner openings 47 have an area that is from about 0.1 mm$^2$ to about 0.5 mm$^2$. Furthermore, in order to balance the need for a visual cue with the need for limited controlled dosing, it is desirable that the number of openings be from about 3 to about 100, such as from about 5 to about 25.

In addition, the inventors have also noted another means of balancing the need for a visual cue with the need for limited controlled dosing is by including outer openings 45 and inner openings 47 of varying size within the skin contactable surface 41. In one embodiment of the invention, the outer openings 45 and inner openings 47 have a size that varies with the disposition of the opening (i.e., the distance of the opening from a center or edge of the skin-contactable surface 41). For example, outer openings 45, which are near to the edge of skin-contactable surface 41, may be relatively small in size, whereas inner openings 47, which are closer to the center of skin-contactable surface 41, may be relatively large in size. The purpose for the difference in size of the outer openings 45 and inner openings 47 is twofold. Firstly, the larger inner openings 47 deliver the majority of the composition to the center of the surface 41 (as opposed to the edge). This tends to reduce "pooling," an undesirable situation wherein too much composition is accumulated near the edge of the stick and portions of the film delivered to the skin are too thick, resulting in flaking of the film after the film dries. Secondly, outer openings 45 provide the visual cue/indication to the user that a sufficient amount of the composition is being delivered to the surface 41. Without the smaller openings, there is a tendency for the user to dose to heavily to surface 41, which also can result in delivering films to the skin that are too thick and are susceptible to flaking.

The difference or gradient in opening size may vary. For example, the diameter or area of the openings may be directly proportional to the distance from the center of the skin-contactable surface 41. Alternatively, the inner openings 47 that are more central may be 30% to about 70% larger than the size of the outer openings 45.

In one embodiment of the invention, the product contains instructions directing the purchaser and/or user to apply the composition to the skin or mucosal tissue as discussed above. The instructions may indicate to apply the composition to the skin or mucosal tissue and to subsequently remove the composition from the skin mucosal tissue such as by washing with soap and water. The instructions may further indicate to avoid touching the skin or mucosal tissue upon which the composition has been applied, such as for a time period of at least about one minute. By waiting a period of time, the product may recover into a durable state.

The instructions may further indicate to apply the tensioning composition to the skin or mucosal tissue at a particular frequency of application, such as at least once per day for at least about 2 weeks. The instructions indicate to apply the tensioning composition at least twice each day for at least about 28 days, such as for at least about 6 weeks, such as at least about 8 weeks.

While the composition may provide improved ability to retain moisture, the instructions may indicate to apply a moisturizer before or after the application of the composition comprising a tensioning polymer. By "moisturizer" it is meant either a composition acting on the barrier function, in order to keep the stratum corneum moisturized. Particular mention may be made of oil-in-water emulsions in which a emollients such oils or other lipid or hydrophobic material comprise a large percentage of the composition, such as greater than about 5%, such as greater than about 10%, such as greater than about 15%. Examples of emollients include, but are not limited to mineral oils, petrolatum, vegetable oils (glycerol esters of fatty acids, triglycerides), waxes and other mixtures of esters, not necessarily esters of glycerol; polyethylene and non-hydrocarbon based oils such as dimethicone, silicone oils, silicone gums, and the like. By applying a moisturizer prior to the tensioning composition, the skin is made more uniform in its suppleness and may provide a more even coating of the tensioning composition.

Furthermore, the instructions may indicate that the composition comprising the tensioning polymer should be applied before makeup, although this is not required. Alternatively, the instructions may indicate to apply the composition after applying make-up. The instructions may further indicate to apply the composition at nighttime, soon before sleeping.

Embodiments of the present invention are particularly advantageous using a composition that has sufficient tensioning to obtain such benefits and is resistant enough to water and humidity such that the film does not irreversibly degrade upon exposure to these challenges, but is not so resistant that the film is difficult to remove by washing. In addition, embodiments of the invention provide for the controlled delivery of films in order to promote easy and uniform application across the skin or mucosal tissue that do not flake.

EXAMPLES

The following is a description of the manufacture of compositions of the present invention. Other compositions of the invention can be prepared in an analogous manner by a person of ordinary skill in the art.

Example 1

The topical composition of table 1 was made by charging a container with deionized water and then adding (in order) ethanol, a pre-mix (A), and a pre-mix (B) until homogeneous. The premix (A) was made by first charging another container with hexylene glycol and adding Kytamer PC until homogeneous. The pre-mix (B) was made by charging still another container with hexylene glycol and adding Flamenco Summit Red and Flamenco Summit Gold. The resulting composition was placed in an applicator such as the one described in above in connection with FIGS. 3-5.

TABLE 1

| Trade Name | CHEMICAL NAME (INCI) | Function | % (w/w) |
| --- | --- | --- | --- |
| Deionized water | Deionized water | Vehicle | 59.25 |
| Hexylene glycol | Hexylene glycol | Vehicle | 6 |
| KYTAMER PC | Chitosan pyrrolidone carboxylic acid | Tensioning polymer | 5 |

TABLE 1-continued

| Trade Name | CHEMICAL NAME (INCI) | Function | % (w/w) |
|---|---|---|---|
| Ethyl alcohol | Ethanol | Vehicle | 20 |
| Advanced Moisture Complex | Glycerin, water, sodium PCA, urea, trehalose, polyquaternium-51, and sodium hyaluronate | Plasticizer | 5 |
| Flamenco summit red | Mica, titanium dioxide | Mattifying agent | 0.02 |
| Flamenco summit gold | Mica, titanium dioxide | Mattifying agent | 0.02 |
| Dow Corning 7-3101 Elastomer blend | Cyclopentasiloxane/diemthicone crosspolymer, dimethicone | Mattifying agent, plasticizer | 5 |

Example 2

The topical composition of table 2 is made by charging a container with deionized water and then adding, in order, ethanol, Kytamer PC, and Advanced Moisture Complex, and a pre-mix until homogeneous. The pre-mix was made by first charging a second container with hexylene glycol and then adding, in order, silica shells, silk, Flamenco red,. and Flamenco Gold until homogeneous.

TABLE 2

| Trade Name | CHEMICAL NAME (INCI) | Function | % (w/w) |
|---|---|---|---|
| Deionized water | Deionized water | Vehicle | 61.09 |
| Hexylene glycol | Hexylene glycol | Vehicle | 6 |
| Kytamer PC | Chitosan pyrolidone carboxylic acid | Tensioning polymer | 6 |
| Ethyl alcohol | Ethanol | Vehicle | 20 |
| Advanced Moisture Complex | Glycerin, water, sodium PCA, urea, trehalose, polyquaternium-51, and sodium hyaluronate | Plasticizer | 5 |
| Flamenco summit red | Mica, titanium dioxide | Mattifying agent | 0.08 |
| Flamenco summit gold | Mica, titanium dioxide | Mattifying agent | 0.08 |
| Silica shells (Kobo) | Silica shells | Mattifying agent | 0.15 |
| Silkall 100 | Silk | | 1.6 |

Example 3

The topical composition of Table 3 is made by charging a container with deionized water, then adding (in order) sodium chloride, glycerin, DC 2501, and ZILGEL and mixing moderately. A premix was formed by combining hexylene glycol and Kytamer, which was then added to the container. Mixing was continued, and the container was heated to a temperature from about 60 C. to about 65 C.

This constituted the water-phase. In a separate container an oil phase was prepared by adding together items 8 through 15. This was heated to a temperature from about 60 C. to about 65 C. The oil phase was then added to the water phase with mixing continued for 5 minutes. Cooling was then applied with moderate mixing.

The composition above is independently placed in an applicator such as one of those described in above in connection with FIGS. 3-5. The composition is dispensed according to the specification and applied to areas in need of wrinkle reduction, such as areas around the eyes.

TABLE 3

| Trade Name | CHEMICAL NAME (INCI) | Function | % (w/w) |
|---|---|---|---|
| Deionized water | Deionized water | Vehicle | 47.08 |
| Hexylene glycol | Hexylene glycol | Vehicle | 10 |
| Kytamer PC | Chitosan pyrolidone carboxylic acid | Tensioning polymer | 5 |
| Sodium chloride | Sodium chloride | Rheology modifier | 0.6 |
| Glycerin | Glycerin | Plasticizer | 1 |
| DC 2501 Cosmetic Wax | Bis-PEG-18 Methyl Ether Dimethyl Silane | Plasticizer | 5 |
| ZILGEL oil | Sodium polyacrylate and PV/MA copolymer | Plasticizer | 4 |
| Dimethicone 245 | Alpha - (Trimethylsilyl-w-methylpoly[oxy(dimethylsilylene)]. | Plasticizer | 10 |
| BHT | Butylated hydroxytoluene | Preservative | 0.07 |
| Vitamin E | Tocopherol acetate | Plasticizer | 0.5 |
| Bisabolol | 1-Methyl-4(1,5-dimethyl-1-hydroxyhex-4(5)-enyl)-cyclohexen-1; 6-Methyl-2-(4-methyl-3-cyclohexen-1-yl)-5-hepten-2-ol | Skin-soothing agent/anti-inflammatory | 0.5 |
| Abil Wax 9801 | Cetyl dimethicone | Plasticizer | 1 |
| Shin Etsu USG-103 | Cyclopentasiloxane and polysilicone-11/polymethylsilsesquioxane composite | Plasticizer | 10 |
| Shin Etsu KSG-210 | Dimethicone PEG-10/15 crosspolymer and dimethicone | Plasticizer, emulsifier, spreading agent | 5 |
| Shin Etsu KP-545 | Cyclopentasiloxane and acrylates/dimethicone copolymer | Plasticizer | 0.25 |

Example 4

The effect of tension-forming polymers on mouse skin was assessed on C57B1/6 8 week old female mice (Jackson Labs, Bar Harbor, Me.), 4 per group. Mice were wax-depilated at the dorsal area and agent application was started 4 days after hair removal. Tensioning polymers Neocryl XK-90 (Neoresins, Frankfort, Ind.) and Polystyrene sulfonate (National Starch & Chemical) were applied to the mouse skins from a 30% water solution and Bovine Serum Albumin (BSA, Intergen, Purchase, N.Y.) was applied to the mouse skins from a 15% water solution. Vehicle (water) was used as a control. Mice were treated once daily, 5 days a week. At week 2 after the start of the treatments mice were sacrificed, skin biopsies from the treated areas were taken, fixed in 10% buffered formalin, put in paraffin blocks and analyzed by H&E staining using standard procedures. Surprisingly, an increase in epidermal thickness was observed in mice treated with tension-inducing polymers (Table 4). BSA showed a minimal effect, and the water vehicle (Control) did not show an effect.

TABLE 4

| Groups | Change vs Control |
| --- | --- |
| Control | 1 +/- 0.11 |
| BSA | 1.1 +/- 0.24 |
| Polystyrene sulfonate | 1.8 +/- 0.47 |
| Neocryl XK-90 | 2.8 +/- 0.31 |

Example 5

Mice were treated with tensioning polymers as in Example 4. At weeks 1 and 3 after the start of the treatments, the mice were sacrificed and skin biopsies were processed for histological analysis. Skin sections were stained with Proliferating Cell Nuclear Antigen (PCNA) using immunohistochemical procedures. Surprisingly, a major increase in the number of proliferating cells was detected in the epidermis of tensioning-polymer-treated mice. This increase in proliferation was documented at 1 and 3 weeks after the start of the treatment (FIG. 1). The numbers of the proliferating cells in epidermis for mice treated with Polystyrene sulfonate and Neocryl XK-90 were 2 to 4 times higher than in the water vehicle or the BSA-treated groups.

Example 6

Mice were treated similar to Example 1 with Neocryl XK-90 in 10% to 30% water solutions. At week 1 after the start of the treatments, the mice were sacrificed and skin biopsies were processed for histological analysis. Precollagen staining demonstrated an increase in new collagen in tensioning polymer-treated mice, but not in the vehicle (water). This increase was dose-dependent, reaching up to an increase of 80% more new collagen at the high dose (30%) treated group.

Example 7

Mouse skin samples from Examples 4 and 6 were frozen in liquid nitrogen, homogenized in RNA Stat (Tel-Test Inc. Friendswood, Tex.) and RNA was isolated following manufacture's protocol. Isolated RNAs were treated with RNase free DNase I (Ambion Inc. Austin, Tex.) at 4 U/100 ug RNA at 37° C. for 1 hour and the DNAse I was removed following manufacturer's protocol. RNAs were further purified by RNeasy columns (Qiagen Valencia, Calif.). cDNAs were synthesized using Superscript first strand synthesis kit (Invitrogen life technologies, Carlsbad, Calif.). PCR primers for mouse PCNA were synthesized according to GenBank sequences (Invitrogen life technologies, Carlsbad, Calif.). Glyceraldehyde-3-phosphate dehydrogenase (GAPDH) primers were purchased from Ambion (Ambion Inc. Austin, Tex.). RT-PCR products were separated on 2% agarose gels stained with ethidium bromide using standard techniques. PCNA mRNA levels were normalized to GAPDH levels. The tensioning polymers Neocryl XK-90 and Polystyrene sulfonate were found to induce PCNA expression in a dose-dependent manner (Table 7).

TABLE 7

| Groups | PCNA/GAPDH ratio |
| --- | --- |
| Control | 1 |
| Neocryl XK-90 10% | 0.75 |
| Neocryl XK-90 20% | 1.23 |
| Neocryl XK-90 30% | 1.6 |
| Polysterene sulfonate 20% | 2.44 |
| Polysterene sulfonate. 30% | 2.76 |

Example 8

Collagen I expression was evaluated using RT-PCR, as described in Example 7. PCR primers for mouse collagen I were synthesized according to GenBank sequences (Invitrogen life technologies, Carlsbad, Calif.). Collagen I mRNA level was normalized to GAPDH level. Tensioning polymers Neocryl XK-90 and Polystyrene sulfonate were found to increase collagen I expression in a dose-dependent manner (Table 8).

TABLE 8

| Groups | COLL/GAPDH ratio |
| --- | --- |
| Untreated | 1 |
| Neocryl XK-90 10% | 0.59 |
| Neocryl XK-90 20% | 1.88 |
| Neocryl XK-90 30% | 3.44 |
| Polysterene Sulfonate 20% | 2.98 |
| Polysterene Sulfonate 30% | 4.27 |

Example 9

An eight-week instrumental study was conducted with 6 women, aged 40-65 with Skin Type I-IV. Epidermal thickening was measured with a Confocal microscope at three sites on the upper inner arm prior to product application. A prototype containing 5% Kytamer PC (Chitosan PCA) was then applied to one of the sites twice a day (morning and night) for eight weeks. A commercially available retinol product was applied to a second site as a positive benchmark. The third site was utilized as an untreated control. Measurements were taken with the Confocal microscope after 2, 4, 6 and 8 weeks of product application. A statistically significant increase in epidermal thickening (microns) versus control was seen for the Kytamer PC treated site at week 6 and 8, as shown in table 4.

TABLE 4

| | 2 Weeks | 4 Weeks | 6 Weeks | 8 Weeks |
| --- | --- | --- | --- | --- |
| Untreated Control | 0.38 | 1.19 | -1.37 | 1.2 |
| Positive Control | 1.58 | 2.95 | 4.74* | 6.58* |
| Kytermer PC | 1.36 | 2.68 | 3.63* | 3.68* |

*= significant (p < 0.05) versus untreated control

While the foregoing is directed to various embodiments of the invention, other and further embodiments may be devised without departing from the basic scope thereof, and the scope thereof is determined by the claims that follow:

the invention claimed is:

1. A method for treating atrophy of skin or mucosal tissue, said method comprising administering to skin or mucosal tissue in need of such treatment a composition in the form of an oil-in-water emulsion comprising at least 15% (w/w) of an oil phase, from about 2 to about 10% (w/w) of a tensioning polymer, from about 40% to about 70% (w/w) water, and from about 10 to about 45% (w/w) of a volatile liquid selected from $C_1$-$C_6$ alcohol wherein said oil phase comprises at least about 40% by weight silicones selected from dimethicone, cyclopentasiloxane, silicone waxes, silicone glycol copolymer wax, and oxy-ethylenated silicone oils and silicone elastomers; said method selected from the group consisting of thickening said skin or mucosal tissue, enhancing extracellular matrix production in said skin or mucosal tissue, and enhancing the barrier function of said skin or mucosal tissue and wherein said tensioning polymer (i) has a contractile force ranging from about 3 g/mg to about 30 g/mg; (ii) has a molecular weight ranging from about 100,000 to about 350,000 daltons; and (iii) is selected from selected from a chitosan polymer.

2. A method of claim 1, wherein said method comprises thickening said skin.

3. A method of claim 1, enhancing the barrier function of said skin.

4. A method of claim 1, enhancing extracellular matrix production on the skin.

5. A method of claim 1, wherein said method comprises enhancing collagen production in said skin.

6. A method of claim 1, wherein said tensioning polymer has a water resistance index from about 0.9 to about 1.9.

7. A method of claim 2, wherein said tensioning polymer has a water resistance index from about 0.9 to about 1.9.

8. A method of claim 3, wherein said tensioning polymer has a water resistance index from about 0.9 to about 1.9.

* * * * *